(12) United States Patent
Carpenter et al.

(10) Patent No.: US 9,458,615 B2
(45) Date of Patent: Oct. 4, 2016

(54) SPRAYING DEVICE

(75) Inventors: Matthew Chace Carpenter, Providence, RI (US); Kenneth Allen Focht, Providence, RI (US); Federico Pasquini, Casalpusterlengo (IT); Davide Pietrasanta, Casalpusterlengo (IT); Andrea Dias Sorze, Casalpusterlengo (IT)

(73) Assignee: Conopco, Inc., Englewood Cliffs, NJ (US)

( * ) Notice: Subject to any disclaimer, the term of this patent is extended or adjusted under 35 U.S.C. 154(b) by 411 days.

(21) Appl. No.: 14/116,139

(22) PCT Filed: Apr. 18, 2012

(86) PCT No.: PCT/EP2012/057043
§ 371 (c)(1),
(2), (4) Date: Dec. 24, 2013

(87) PCT Pub. No.: WO2012/156170
PCT Pub. Date: Nov. 22, 2012

(65) Prior Publication Data
US 2014/0115765 A1    May 1, 2014

(30) Foreign Application Priority Data
May 13, 2011   (EP) ..................................... 11166060

(51) Int. Cl.
*E03D 9/02*     (2006.01)
*E03D 9/00*     (2006.01)
(Continued)

(52) U.S. Cl.
CPC ................. *E03D 9/005* (2013.01); *A61L 9/14* (2013.01); *B05B 9/0861* (2013.01); *A61L 2/22* (2013.01); *A61L 2209/111* (2013.01); *A61L 2209/133* (2013.01); *B05B 3/02* (2013.01)

(58) Field of Classification Search
CPC ........... E03D 9/005; A61L 9/14; A61L 2/22; A61L 2209/111; A61L 2209/133; B05B 9/0861; B05B 3/02
USPC ............. 4/222, 223, 224; 134/167 R, 169 R; 239/263.1, 263.3, 67, 69, 70, 97, 225.1
See application file for complete search history.

(56) References Cited

U.S. PATENT DOCUMENTS

| 298,091 A | 5/1884 | Hubbard et al. |
| 3,579,721 A | 5/1971 | Kaltenbach |

(Continued)

FOREIGN PATENT DOCUMENTS

| EA | 1559436 A1 | 3/2005 |
| EP | 1467820 B1 | 10/2004 |

(Continued)

OTHER PUBLICATIONS

PCT International Search Report in PCT application PCT/EP2012/057043, mailed Jul. 30, 2012.

(Continued)

*Primary Examiner* — J. Casimer Jacyna
*Assistant Examiner* — Benjamin R Shaw
(74) *Attorney, Agent, or Firm* — Greenberg Traurig, LLP (57) ABSTRACT

The present invention relates to a automated spraying device for spraying an enclosure with a liquid cleanser, the device having,—a reservoir (16) for containing the liquid cleanser,—a pump (14) in fluid communication with the reservoir, and—a movable spray head (15) having an outlet orifice through which cleanser from the reservoir can be expelled during operation of the pump if there is such liquid cleanser in the reservoir. Said spraying device also contains an electrical motor drive mechanism (12) for sequentially operating th pump (14) and moving the spray head (15) to modify the direction of the spray there from, such that the spray head is not simultaneously spraying and moving. Furthermore, the spray head is suitable for producing an aerosol whereby the Dv50 of the aerosol is in the range of from 30 to 70 micron.

13 Claims, 5 Drawing Sheets

(51) Int. Cl.
*A61L 9/14* (2006.01)
*B05B 9/08* (2006.01)
B05B 3/02 (2006.01)
A61L 2/22 (2006.01)

(56) References Cited

U.S. PATENT DOCUMENTS

| | | | | |
|---|---|---|---|---|
| 4,272,018 A | * | 6/1981 | Hickson | B05B 3/02 239/225.1 |
| 5,497,944 A | | 3/1996 | Weston et al. | |
| 5,896,871 A | * | 4/1999 | Larsen | B05B 3/02 134/167 R |
| 5,906,009 A | | 5/1999 | Sakar | |
| 5,926,099 A | | 7/1999 | Unum et al. | |
| 6,102,298 A | | 8/2000 | Bush et al. | |
| 6,971,549 B2 | | 12/2005 | Leifheit et al. | |
| 7,021,494 B2 | | 4/2006 | Mazooji et al. | |
| 7,021,555 B2 | | 4/2006 | Bagnall | |
| 7,337,989 B1 | * | 3/2008 | Penner | A47K 3/281 239/210 |
| 9,016,598 B2 | * | 4/2015 | Ikushima | B05B 3/026 239/225.1 |
| 2003/0168524 A1 | | 9/2003 | Hess et al. | |
| 2004/0026531 A1 | | 2/2004 | Sanada et al. | |
| 2004/0050959 A1 | * | 3/2004 | Mazooji | B05B 9/0861 239/263.1 |
| 2004/0206772 A1 | * | 10/2004 | Leifheit | A47K 3/281 222/83 |
| 2004/0217197 A1 | * | 11/2004 | Mazooji | A47K 3/281 239/302 |
| 2004/0256482 A1 | | 12/2004 | Linden | |
| 2005/0043203 A1 | | 2/2005 | Barnabas et al. | |
| 2005/0103891 A1 | | 5/2005 | Abergel et al. | |
| 2007/0051827 A1 | | 3/2007 | Shen et al. | |
| 2007/0204388 A1 | * | 9/2007 | Zyskowski | E03D 9/007 4/228.1 |
| 2010/0031982 A1 | * | 2/2010 | Hornsby | E03D 9/005 134/169 R |
| 2010/0133362 A1 | * | 6/2010 | Fahy | B05B 3/02 239/548 |
| 2010/0257662 A1 | * | 10/2010 | Huang | A47K 13/302 4/223 |
| 2011/0073675 A1 | * | 3/2011 | Wolosuk | A01M 13/00 239/210 |
| 2013/0025038 A1 | * | 1/2013 | Frey | B05B 17/0607 4/222 |
| 2014/0008457 A1 | * | 1/2014 | Bosua | B05B 15/025 239/104 |
| 2015/0231340 A1 | | 8/2015 | Pumphrey et al. | |

FOREIGN PATENT DOCUMENTS

| | | |
|---|---|---|
| GB | 2456491 A | 7/2009 |
| JP | 2005052257 | 3/2005 |
| WO | WO9917650 A1 | 4/1999 |
| WO | WO9963877 A1 | 12/1999 |
| WO | WO0001423 A1 | 1/2000 |
| WO | WO2010047800 A2 | 4/2010 |
| WO | WO2011061478 A1 | 5/2011 |
| WO | WO2011091002 A1 | 7/2011 |
| WO | WO2011124277 A1 | 10/2011 |
| WO | WO2011156556 A1 | 12/2011 |
| WO | WO2012114230 A1 | 8/2012 |
| WO | WO2012156170 A1 | 11/2012 |

OTHER PUBLICATIONS

International Preliminary Report on Patentability in PCT application PCT/EP2012/057043, dated Aug. 18, 2013.
PCT International Written Opinion PCT/EP2012/057043.
EP Search Report in EP application EP 11 16 6060, dated Oct. 12, 2011.

* cited by examiner

SPRAYING DEVICE

FIELD OF THE INVENTION

The present invention relates to a cleaner spraying device for automatically spraying an enclosure. In particular, the invention relates to a cleaner spraying device which is suited for automatically cleaning a toilet bowl, more specifically for treatment of micro-organisms and viruses that become airborne in the inner volume of the toilet bowl during flushing.

BACKGROUND OF THE INVENTION

It is well known that every time the toilet is flushed after use, thousands of bacteria and virus particles are catapulted into the air, travelling as far as two meters or more out of and up from the toilet bowl as a fine invisible mist. An existing hypothesis refers to the greatest bacterial mist dispersal occurring not during the initial moments of the flush, but rather once most of the water has already left the bowl.

The bacterial mist can remain airborne for over two hours, floating around in the air and spreading over the room to finally settle on and thus contaminating the available surfaces around the toilet. This spread of faeces originating bacteria and/or viruses over the bathroom is undesirable with respect to hygiene and could even cause serious health problems. Examples of surfaces on which deposition of pathogenic micro-organisms or viruses is highly undesirable are toothbrushes, hairbrushes, light switches, and the toilet paper.

There is thus a need to prevent the spread of active airborne micro-organisms and viruses from the toilet after flushing, in particular when pathogenic micro-organisms are involved.

Several attempts have been made to solve the problem of these airborne micro-organisms and viruses.

U.S. Pat. No. 5,906,009 discloses a toilet bowl that has gases and bacteria or virus-laden mist removed directly therefrom by an air evacuation system, both during and after use of the toilet. The disadvantage of such a solution is that it requires a special toilet bowl and a separate and relatively expensive air evacuation system.

WO00/01423 discloses a method of disinfecting or sanitising a space occupied by airborne micro-organisms and/or viruses, which method comprises directing into the space unipolar charged liquid droplets from a spray device containing a disinfecting or sanitising composition. It is not disclosed that the space occupied by airborne micro-organisms and/or viruses is the space inside the toilet bowl. Since the preferred spray device is a domestic pressure-spraying device capable of being hand held, it is evident that the space referred to in this document is open to the user. The use of such a hand-held spraying device has several disadvantages. First of all it is cumbersome to use compared to an automatic sprayer. Secondly, the user is in the same space as the sprayed droplets, and will undoubtedly be in contact with at least a small part of the sprayed composition. Thirdly, since the space containing the airborne micro-organisms and/or viruses is open to the user it is very likely that the user will be contacted by these micro-organisms and/or viruses.

EP-B-1,467,820 discloses an automated sprayer for spraying an enclosure with a liquid cleanser, whereby the sprayer contains a reservoir for holding the liquid cleanser, a pump in fluid communication with the reservoir and a movable spray head having an outlet orifice through which cleanser from the reservoir can be expelled during operation of the pump. The sprayer disclosed by this document also contains an electric motor drive mechanism for operating the pump and also simultaneously moving the spray head.

Although it is mentioned in EP-B-1,467,820 that the enclosure could suitably be a toilet bowl (with the lid in closed position), the automated sprayer disclosed in said document is mainly for use in bath and shower enclosures.

It is an object of the present invention to provide a device that is capable of eliminating within a toilet bowl, the airborne micro-organisms and viruses generated during flushing of the toilet. In addition, it is an object of the current invention to provide a device that prevents the airborne micro-organisms and viruses generated during flushing to spread around the bath room.

A further objective of the invention is to provide a device that generates an aerosol of a disinfecting or sanitising fluid. Another objective of the invention is to provide a device that properly sanitizes the toilet after use.

Another object of the invention is to provide a device that reduces the chance that a user of the toilet comes in contact with airborne micro-organisms and viruses and/or disinfecting or sanitising fluid. Another objective of the invention is to provide a device that avoids the user having to reach into the toilet bowl to (re-)place the device. A further objective of the invention is to provide a device that is easy in use.

Another objective of the invention is to provide a device that is small and compact. Another objective of the invention is to provide a device that for environmental and economic reasons only consumes a small amount of a disinfecting or sanitising fluid per use. Another objective of the invention is to provide a device that can be easily re-filled. Another objective of the invention is to provide a device that will work automatically. Another objective of the invention is to provide a device that will only work when the toilet lid is closed. Another objective of the invention is to provide a device that will only be activated at the most appropriate time. Finally, it is an objective of the invention to provide a device that will remain active for an effective amount of time.

It was surprisingly found that one or more of the above objects can be achieved by an automated spraying device according to the present invention, said device being suitable for spraying an enclosure, in particular a toilet bowl. More in particular, it was found that airborne micro-organisms and viruses generated during flushing of the toilet after use can be significantly reduced within the toilet bowl by using the device of the invention, thus avoiding contamination of any surfaces outside the toilet bowl and at the same time sanitizing the inside of the toilet bowl itself. Furthermore, it was found that the inner surface of a toilet bowl including the area under the rim thereof can be properly sanitized by the device of the invention. It is considered that this is the beneficial effect of the aerosol which said device is able to produce.

DEFINITION OF THE INVENTION

Accordingly, in one aspect the present invention provides an automated spraying device for spraying an enclosure with a liquid cleanser, the device having,
 a reservoir suitable for containing the liquid cleanser,
 a pump in fluid communication with the reservoir,
 a movable spray head having an outlet orifice through which cleanser from the reservoir can be expelled during operation of the pump if there is such liquid cleanser in the reservoir, characterised in that the spraying device also contains an electrical motor drive mechanism for sequentially operating the pump and moving the spray head to modify the direction of the spray there from, such that the spray head is not simultaneously spraying and moving, and in that the spray head is suitable for producing an aerosol whereby the Dv50 of the aerosol is from 30 to 70 micron, preferably from 40 to 60 micron.

Preferably, the spraying device of the invention contains a gearing system which has a configuration such that flow of liquid cleanser to the spray head is interrupted when the spray head is moved by action of the motor drive mechanism. Furthermore, it is desirable that the motor drive mechanism can rotate the spray head, preferably over an angle of 360 C.

In a second aspect, the present invention provides a method for disinfecting and sanitizing the inner volume of a toilet bowl containing airborne micro-organisms and/or viruses generated during and/or after flushing, said method comprising the steps of attaching a spraying device of the invention to the bottom side of a toilet lid, closing the lid, flushing the toilet, and actuating the device. Most preferably, the spraying device is actuated by carrying out the following consecutive steps:

(a) spraying a predetermined amount of liquid cleanser, followed by, (b) rotating the spray head, preferably over an angle of 72 C, and repeating steps (a) and (b) at least 5 times.

Preferably, the above steps (a) and (b) are repeated for at most 15 times, more preferably at most 10 times.

In a third aspect, the invention provides the use of a device of the invention, for disinfecting and/or sanitizing the air present in the inner volume of a toilet bowl after flushing said toilet.

DETAILED DESCRIPTION OF THE INVENTION

For the purpose of this invention an aerosol is a gaseous or airborne cloud of particles. These particles are either a solid or liquid or a combination of both. The particles are larger than a molecule but small enough to allow them to remain suspended in the atmosphere for a certain amount of time (e.g. over the length of a toilet flush). The average diameter of the particles falls within the range of from 30 to 70 μm.

Preferably the average diameter of the particles falls within the range of from 40 to 60 μm as measured using standard particle size measurement apparatus (ex Malvern Spraytec Dv50 measurement) and sprays at 25° C. taking an average of 3 repeat measurements.

The particle size specification used in this invention is the volume median particle diameter (Dv50). This Volume Median Diameter is the diameter of a single droplet, whose volume, when multiplied by the total number of droplets in the spray, is found to equal the total spray volume. The volume median diameter is calculated by dividing the total spray volume in half (50% of the total volume will have larger diameter droplets and 50% will have smaller diameter droplets).

The aerosol generated may be described by the rate of delivery and the shape of the cone of particles leaving the device. Preferably the rate of delivery is from 0.001 to 3.0 g/second, more preferably 0.005 to 2.5 g/second.

Most preferable is a delivery rate of 0.0075 to 2.0 g/second. The cone formed by the aerosol may have a wide angle nearing 180° but is preferably less than 90°, more preferably less than 75°, still more preferably less than 60°, even more preferably less than 35°, most preferably less than 25°. The cone angle may be measured from still photographs of the cone taken with a Nikon SLR D80 camera. The cone angle is measured from one edge of the cone to the other. The spray pattern of the created cone may be hollow but a full cone spray pattern with a uniform distribution throughout the cone is preferred.

The term sanitising as used in this application refers to a lower level of germ control, killing about 50 to 75% of the germs present on a surface or in the air.

For the purposes of this patent, disinfecting can be understood as a higher level of germ control than meant with sanitising (i.e. over 75% germ kill). Under controlled conditions a disinfecting solution provides a 100,000 fold or better reduction in the number of viable micro-organisms (using a specific culture that is treated with the disinfecting solution for an appropriate time period, normally 5 minutes). This is generally known as a '5 log reduction'.

The inner volume of the toilet bowl is defined by the space enclosed by the toilet bowl, the water in the bowl, and the toilet lid when the lid is in the closed (lowered) position.

The bottom-side of the toilet lid is the side of the lid that faces the inner side of the toilet bowl when it is in its closed (lowered) position.

The spray head is preferably suitable for generating the aerosol, by breaking up the liquid cleanser into aerosol sized particles having an average diameter falling within the desired range(s). For obtaining an aerosol with an average particle size according to the present invention at a rate of delivery through the spray head of 0.001 to 3.1 gr/sec, the spray head preferably contains an orifice having a diameter of 0.15-0.3 mm.

It is also preferred that the spray head splits the incoming fluid flow into separate fluid streams which flow tangentially into a swirl chamber, so as to create a fluid vortex just prior to spray discharge through the orifice.

When flowing through the orifice, the flow of cleaning fluid accelerates, whereby it breaks up first into fluid ligaments and subsequently into droplets.

Apart from the size of the orifice and the design of the spray head, the mass flow rate there through and the pressure inside the spray head may also affect the particle size of the aerosol.

It has been found that said mass flow rate is desirably 0.5-1 ml/second for obtaining the above rate of delivery, whereas said pressure is suitably 3-7 bar.

Other factors that may affect the average particle size of the aerosol are the density and the viscosity of the cleaning fluid which are preferably about 1 kg/litre respectively 1-10 centipoise.

When in operation, the disinfecting or sanitizing liquid cleanser is transferred from the reservoir to and/or through the spray head by the action of a pump. Suitable pumps may be selected from pneumatically or electrically operated pumps. Preferably, the pump is electrically operated. By way of non-limiting example such an electrically operated pump may be a gear pump, an impeller pump, a positive displacement pump, a rotary pump, a piston pump, a screw pump, a peristaltic pump, a diaphragm pump, or any other pump which may be incorporated into the liquid cleanser spraying device.

The means for transferring the fluid also comprises the necessary tubing or conduits for transferring the fluid from the reservoir to the spray head.

The spraying device of the invention preferably contains means for attaching it to the bottom side of the lid of a toilet. Said means cover any aid, appliance or tool that may be used to secure the device temporarily or permanently to the toilet lid. Non limiting examples of such means are a layer or drop of adhesive, double sided tape and Velcro. It is however, also possible to use a clamp, a hook, a screw, a bayonet fitting or similar means to attach the device to the lid. Alternatively, a combination of different securing aids, appliances and/or tools might be used.

The three main sub-units of the spraying device (i.e. the reservoir for holding the liquid cleanser, the spray head for generating the aerosol and the pump) may all be placed on the bottom-side of the toilet lid at different discrete locations. It is also possible that two of these sub-units are placed on the lid together while the third sub-unit is placed on the lid at a distance from the other two. Preferably the device is compact and may be placed on the bottom-side of the lid as a single unit containing all three main sub-units.

It is preferred that the spraying device can only operate for spraying the toilet bowl and generating the aerosol when the lid is in the closed position. This may preferably be achieved by using one or more sensors that detect the position of the lid and will only allow activation of the device as long as it is detected that the lid is in the closed (lowered) position or once it was detected that the lid has been closed. Non limiting examples of sensors that may be used to detect the position of the lid are, motion sensors, position switches (like a mercury switch, or a simple metal ball that moves from a first (inactive) position to second (active) position upon repositioning of the toilet lid), light sensors, sound sensors, pressure sensors and weight sensors.

Optionally the signal from the sensor(s) indicating that the lid is in the closed position may be relayed to a timer. This timer controls the delay with which the device starts spraying and creating the aerosol after it has been detected that the lid is in the closed position. Preferably, the timer also controls the duration for which the device dispenses the aerosol.

In another embodiment the device may make use of one or more sensors for detecting that the toilet is being flushed. Such sensors may be used to detect the start of the flush, the flushing cycle it self and/or the end of the flush. Depending on the type of sensors used, these may for example be placed in or on the button for activating the flush, under the rim of the toilet bowl, in the reservoir holding the flush water, on the toilet lid, or any other position suitable for detecting the flush. Non-limiting example of sensors that may be used for detecting the flush are, motion sensors, pressure sensors, sound sensors, position sensors, humidity sensors and water level sensors.

The signal of the sensor(s) for detecting the flush is preferably relayed to the timer allowing the timer to control the start and duration of the spraying operation and aerosol generation by the dispensing device in relation to the advancement of the flushing cycle.

Most preferably the signal(s) from the sensor(s) detecting the position of the lid as well as the signal(s) from the sensor(s) detecting the flush are relayed to the timer. This allows a timer/controller to activate the dispensing device at a time and for a duration that is closely related to the advancement of the flush, but only when a signal has been (or is being) received that the lid is (still) in the closed position.

The operation of the spraying device may last for duration of time, preferably from 1 to 60 seconds, most preferably from 10 to 40 seconds. Preferably the spraying and moving of the spray head starts on the initiation of the flush. Preferably up to 30 to 60 seconds post initiation, most preferably starting from initiation of the flush up to 15 to 20 seconds post initiation.

The device contains an electric power source for enabling the electric motor drive mechanism to sequentially operate the pump and move the spray head according to the invention. In addition to the pump and the spray head for generating the aerosol, the sensors and the timer/controller may also be fed by the electric power source. The electric power may be supplied by one or more batteries, such as single-use batteries or rechargeable batteries, one or more photovoltaic cells, the main supply or combinations thereof. An example of such a combination may be the combination of one or more batteries, with one or more photovoltaic panels. Alternatively, the power supply provided may be a combination of one or more batteries and/or one or more photovoltaic panels which are used to generate a charge which is stored in one or more capacitors, the discharge of such capacitors is used to supply the electric power.

Preferably, the device is fed by one or more single-use or rechargeable batteries.

Preferably, the device is constructed and placed on the lid in such a way that it is easy for the user to re-load the device with the disinfecting or sanitising cleansing fluid. One option of reloading the device is by re-filling the reservoir with the disinfecting or sanitising fluid without having to remove the reservoir from the device and/or lid. A second option of reloading the device is by removing the reservoir from the device and/or lid, re-filling the removed reservoir, followed by placing the re-filled reservoir back in the device and/or on the lid. A third and preferred option of reloading the device is by replacing the empty reservoir by a second (loaded) reservoir (i.e. a re-fill cartridge).

The volume of the reservoir may fall within the range of from 5 to 200 ml, preferably from 10 to 100 ml, more preferably from 15 to 60 ml, most preferably from 30 to 50 ml.

Optionally, when using a new re-fill cartridge, this re-fill cartridge may be configured such that it also contains one or more fresh batteries as the electric power source. The user may thus, very conveniently, replenish the disinfecting and/or sanitising cleanser fluid and the power source simultaneously.

As is clear from the above description, the device can be constructed in many different ways while still delivering an effective aerosol. Depending on the chosen system for generating energy, the dimensions of the spray head and the composition of the disinfecting and/or sanitising cleansing fluid, the preferred rate of delivery and the particle size of the aerosol will vary.

Preferably, the disinfecting or sanitising liquid cleanser used in the device of this invention comprises at least one compound selected from the group comprising biocides, fragrances, surfactants, solubilizers or hydrotropes, colorants and odour immobilisers.

Biocides

Suitable biocides may be selected from the group consisting of oxidising biocides, low molecular weight alcohols, cationic materials, hydrogen ion donators with a starting pH (i.e. pH of disinfecting or sanitising fluid prior to spraying) below pH 3, substituted phenolic biocides, essential oils and metal ions having biocidal properties.

Suitable oxidising biocides may be selected from the group consisting of materials yielding a hypochlorite or hypobromite species on aqueous solution (for example alkali metal and alkaline earth metal hypochlorites and hypochlorite addition products such as the hetrocyclic N-bromo and N-chloro imides (specific examples being sodium hypochlorite, potassium hypochlorite, calcium hypochlorite, magnesium hypochlorite, sodium hypobromite, potassium hypobromite, calcium hypobromite, magnesium hypobromite, sodium bromide, sodium dichloroisocyanurate, potassium dichloroisocyanurate, trichloroisocyanuric acid)), hydantoins (such as 1,3-dichloro-5,5-dimethylhydantoin, N-monochloro-5,5-dimethylhydantoin, N-bromo-N-chloro-5,5-dimethylhydantoin, N-bromo-N-chloro-5-ethyl-5-methylhydantoin), materials liberating free iodine in aqueous solution (such as povidone iodine, lugols iodine, tincture of iodine), chlorine dioxide, chlorine dioxide producing materials, peroxides (such as hydrogen peroxide) and peroxygen generators (examples being peracetic acid, sodium percarbonate, sodium perborate, potassium percarbonate, sodium percarbonate).

Suitable low molecular weight alcohols may be selected from the group consisting of methanol, ethanol, propanol and butanol.

Suitable cationic materials may be selected from the group consisting of cationic polymers (such as polyhexamethylene biguanide (PHMB) and its salts) and quaternary ammonium compounds having at least one C8-22 aliphatic or alkyl aromatic group (e.g. alkyl benzyldimethyl-ammonium chloride, didecyldimethylammonium chloride, cetyltrimethylammonium chloride).

Suitable hydrogen ion donators with a starting pH below pH 3.0, more preferably below pH 1.3 and even more preferably below pH 1.1 may be selected from the group consisting of mineral acids (such as hydrochloric acid, sulphuric acid, phosphoric acid and nitric acid) and organic acids (such as formic acid, citric acid, lactic acid and acetic acid).

Suitable substituted phenolic biocides may be selected from the group consisting of substituted phenolic biocides where substitution occurred with one or more halogen atoms or one or more alkyl groups (examples including ortho-, meta- and para-cresols, ortho phenyl phenol, xylenols, trichlorophenols and more complex materials such as 4-chloro-3:5 dimethyl phenol (PCMX)).

Another very suitable type of biocide is benzalkomium chloride.

Suitable essential oils with known antimicrobial properties may be selected from the group consisting of Sideritis or Greek Mountain Tea, Oregano oil, Tea tree oil, Mint oil, Sandalwood oil, *Nigella sativa* oil, Lavender oil, Lavender oil, Lemon oil, Neem oil, *Eucalyptus* oil, Peppermint oil, Cinnamon oil and Thyme oil. Suitable metal ions having biocidal properties may be selected from the group consisting of silver ions, copper ions, zinc ions and salts liberating these silver, copper or zinc ions.

Suitable amounts of biocides depend on the nature of the biocide and are usually easily determined by a skilled person. However general guidelines are more than 75 wt %, more preferably more than 90 wt % for low molecular weight alcohols. Suitable amounts for substituted phenolic biocides, cationic materials and/or oxidising biocides ranges from 0.1 wt % to 30 wt %, more preferably from 0.5 wt % to 15 wt %, even more preferably from 1 wt % to 9 wt % and most preferably from 2 wt % to 5 wt %.

Fragrances

For the purpose of this invention any type of fragrance compositions and/or aromatic oil may be suitable, particularly those with high solubility in water and/or alcoholic solutions, most particularly those stable in the presence of chlorine bleach or bleaching agents or oxidizing agents. Suitable amounts of fragrances range from 0.01 wt % to 10 wt %, more preferably from 0.1 wt % to 5 wt %, even more preferably from 0.5 wt % to 3 wt % and most preferably from 1 to 2 wt %. The level of fragrance may vary whether the composition has an aqueous base or a non-aqueous base. For aqueous based compositions the level of fragrance is usually higher than for non-aqueous based compositions. A composition is aqueous based if it comprises more than 50 wt % of water.

Surfactants

Suitable surfactants may be selected form the group consisting of anionic surfactants (like for example sulphates (e.g. C10-C18 laureth and pareth with ethylene oxide units 0 to 3 sulphated), sulphonates (e.g. alkyl benzene sulphonated with MMW 300-350), carboxylates (e.g. alkali metal and alkaline earth metal salts of fatty acids C10-C18)), non-ionic surfactants (e.g. fatty alcohol ethoxylate having HLB 7 to 20, sorbitan ethoxylate having HLB 7 to 20, alkyl poly glycosides with carbon chain between C8-C16 with DPI 1.4-1.6 and HLB 11.6 to 13.6, n-alkyl pyrrolidones with HLB 3 to 6), cationic surfactants (like quaternary ammonium compounds having at least one C8-22 aliphatic or alkyl aromatic group (e.g. alkyl benzyldimethyl-ammonium chloride, didecyldimethylammonium chloride, cetyltrimethyl-ammonium chloride) and zwitterionic surfactants (e.g. dimethyl-alkyl amine oxide with carbon chain C12-C18).

Suitable amounts of surfactants range from 0.01 wt % to 30 wt %, more preferably from 2 wt % to 25 wt %, even more preferably from 5 wt % to 15 wt % and most preferably from 7 to 10 wt %.

Solvents or Hydrotropes

Suitable solvents (or hydrotropes) may be selected from the group consisting of low molecular weight alcohols (containing 2 to 4 Carbon atoms, e.g. primary, secondary or tertiary alcohols like ethanol, isopropanol, tert-butanol), ethylene and propylene glycols and their mono C1-C6 ethers (e.g. dimethoxyethane (glyme)), low molecular weight alcohol amines (e.g. monoethanolamina), and glycerol or its derivatives (like glycerides). For aqueous based compositions suitable amounts of solvents range from 0.01 wt % to 30 wt %, more preferably from 2 wt % to 25 wt %, even more preferably from 5 wt % to 15 wt % and most preferably from 7 to 10 wt %. For non-aqueous based compositions suitable amounts of solvents range from 25 wt % to 95 wt %, more preferably from 40 wt % to 90 wt %, even more preferably from 50 wt % to 80 wt % and most preferably from 60 to 75 wt %. It should be understood that for the purpose of this invention when low molecular alcohols are used as biocides that they are counted as solvents or hydrotropes.

Optional Other Components:

Optional other components may be selected from the group consisting of salts, dyes, and other benefits' agents like odour removal/masking ingredients (e.g. Zn ricinoleate), nebulised/atomized particle size modulators which include surface tension modifiers (static & dynamic), and polymers & rheology modifier (synthetic and/or natural)

The overall disinfecting or sanitising fluid may be a water based composition or a non aqueous based composition.

A preferred embodiment of the present invention may use a biocide selected from the group of methanol, ethanol, propanol, butanol, PHMB, benzalkonium chloride and hypochlorite.

The preferred disinfecting or sanitising fluid contains one of the following biocides at the specified concentrations (wt %):

Hypochlorite concentration: from 0.05 to 4%, preferably from 0.1 to 3%;

Ethanol: from 25 to 95%, preferably from 75 to 95%;
PHMB: from 1 to 20%, preferably 5 to 20%, more preferably 10-20%;
Benzalkonium chloride: from 0.75 to 3%

To achieve optimal sanitising action of airborne bacteria it is critical to deliver an effective amount of a suitable biocide into the airspace to be sanitised.

Figure 1:
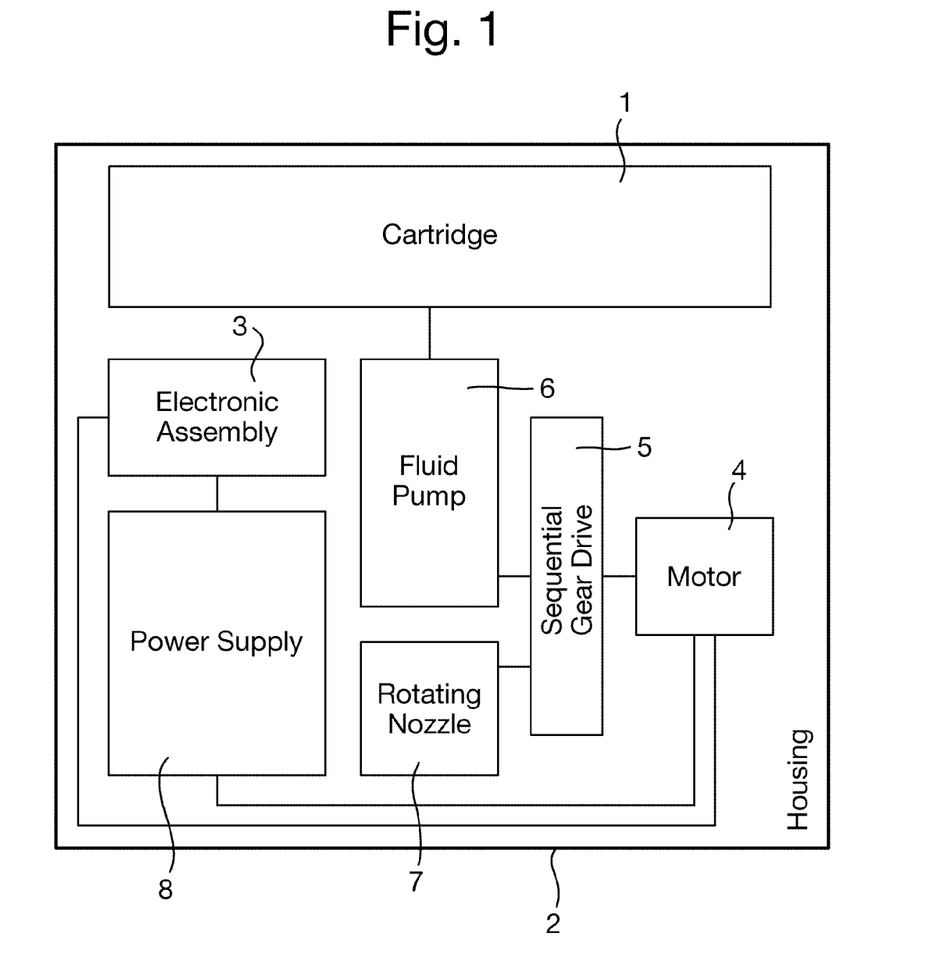
Figure 2:
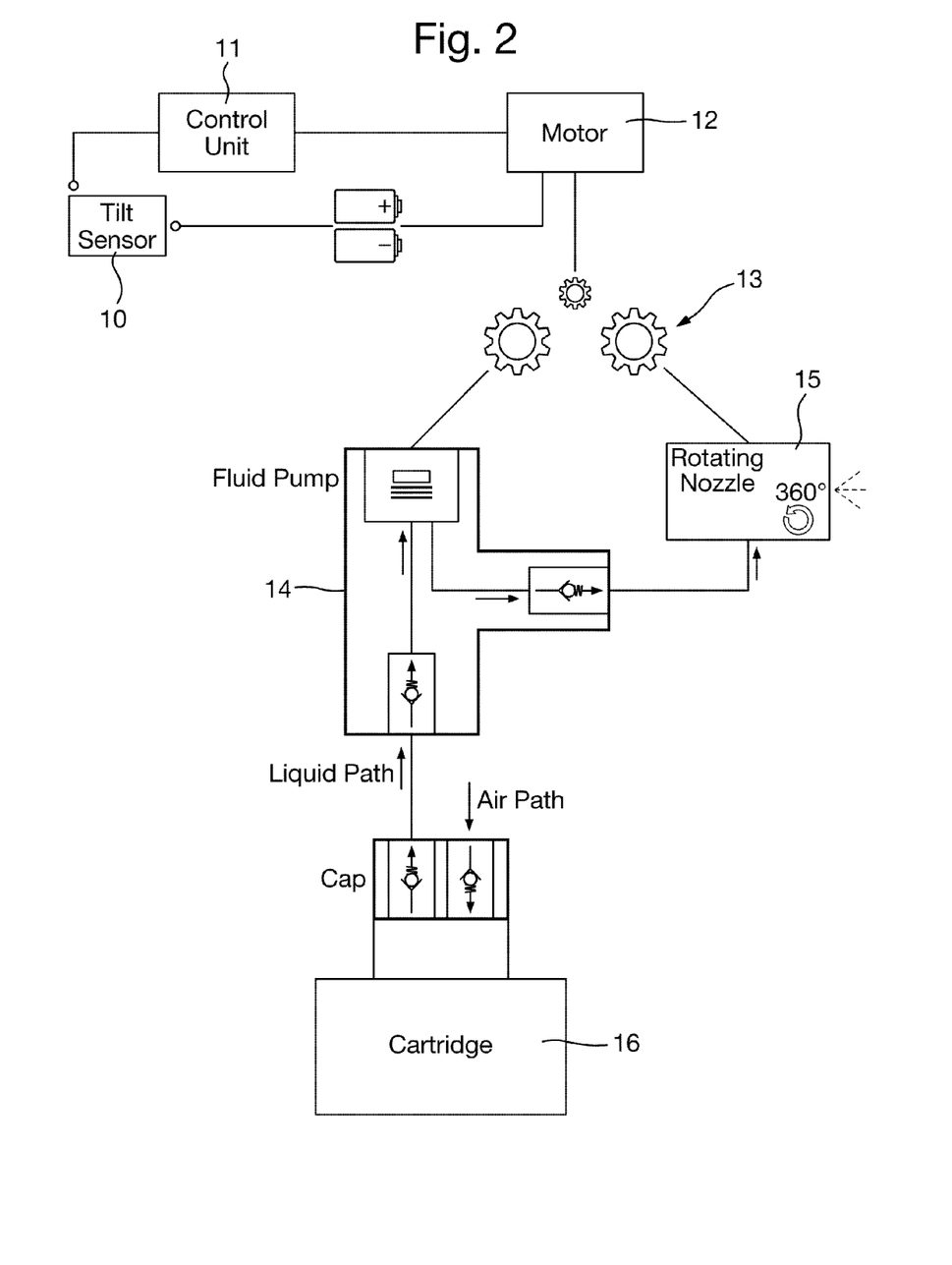

A suitable way to use the device may be as follows:

The user may place the device on the bottom-side of the toilet lid. In case the device makes use of remote sensors these may be placed on the appropriate positions of the toilet as well. The device and any (optional) remote sensors only need to be placed in position once, after which the device may be used for between 2 and 2000 activations, preferably between 5 and 200 activations, more preferably between 5 and 100 activations. After using the toilet, the user closes the lid and subsequently flushes the toilet. Following these actions the spraying device may automatically be activated: as a result, it starts to sequentially dispense the disinfecting and/or sanitising fluid as an aerosol into the inner volume of the toilet bowl and rotate the spray head. The device may remain active until enough fluid is dispensed to effectively kill more than 50%, preferably more than 75%, more preferably more than 90%, more preferably at least 99%, most preferably more that 99.9% of the airborne micro-organisms and/or viruses that were created during the flush.

Preferably the aerosol is forced to flow away from the spraying device into the toilet bowl in such a way that the aerosol particles may spread evenly over the whole inner volume of the toilet bowl. Preferably, it is avoided to cover one side of the inner volume of the toilet bowl more than its opposite side. An aerosol spray that is biased to cover one side of the inner volume of the toilet bowl more than its opposite side might cause a significant difference in concentration of disinfecting or sanitising aerosol droplets from one part of the bowl volume to the other. This may cause the airborne bacteria and viruses present in the area where there is a low(er) concentration of disinfecting or sanitising aerosol droplets to survive the treatment.

The spraying device may be placed anywhere on the bottom-side of the toilet lid as long as the emitted aerosol particles can cover the whole inner volume of the toilet bowl without creating a significant difference in concentration of disinfecting or sanitising aerosol droplets from one part of the bowl volume to the other. Preferably the spraying device is placed more or less in the middle of the lid.

In order to cover the whole inner volume of the toilet bowl without creating a significant difference in concentration of disinfecting or sanitising aerosol droplets from one part of the bowl volume to the other, the direction wherein the aerosol is emitted by the spray head is related to the position of the dispensing device on the lid. Preferably the spray head is rotatable over 360 C.

The aerosol particles remain suspended in the air for an effective amount of time. This allows them to diffuse from the point of entering the inner volume of the bowl (evenly) in all directions towards the bowl surface including the space under the rim. The aerosol particles may thus eliminate the airborne micro-organisms and/or viruses (evenly) over the whole inner volume of the bowl and may remain effective against airborne micro-organisms and/or viruses all the time they remain suspended in the air. The delivery of the disinfecting and/or sanitising aerosol in combination with the time the created aerosol remain suspended in the air is preferably controlled in such a way that an effective number of aerosol particles remain suspended in the air until the end of the flush (i.e. for as long as airborne bacteria and/or viruses may be created).

Without wishing to be bound by theory we believe that on top of the kill of airborne micro-organisms and viruses in the air, the present invention has an additional benefit. We believe that the cloud of disinfecting and/or sanitising aerosol particles that is entering the volume of the toilet bowl from the top downwards pushes the airborne micro-organisms and viruses back to the flush water and/or to the surface of the bowl, away from the toilet bowl opening, thus preventing them from escaping the volume of the toilet bowl.

After a certain amount of time the disinfecting and/or sanitising aerosol particles settle on the interior surface of the toilet bowl (including the surface under the rim) and partly dissolve in the remaining flush water. The deposited and/or dissolved disinfecting and/or sanitising fluid remains active and will disinfect and/or sanitise the interior surface of the toilet bowl and/or the remaining flush water as well.

DESCRIPTION OF THE DRAWINGS

FIG. 1 shows a schematic drawing of the main components of a spraying device of the present invention.

Said spraying device includes as main components a cartridge assembly or reservoir (1) for holding a liquid cleaning solution, a housing assembly (2) comprising a mounting plate system for connecting the spraying device to the inner surface of a toilet lid and an electronic assembly (3) comprising a tilt sensor, a counting switch and a safety switch for controlling the activation and duration of the spray cycle. Other main components of the spraying device schematically shown in FIG. 1 are an electric motor (4) for driving a sequential gear drive assembly (5), said gear drive assembly for sequentially operating a fluid pump (6) and a rotatable nozzle (7), said fluid pump (6) for drawing in, pressurizing and releasing the cleaning solution in a predefined amount, said rotatable nozzle (7) for atomizing the cleaning solution into a sprayed aerosol, and finally a power supply comprising two AA batteries for providing the required power to operate the device.

FIG. 2 shows a flow chart relating to the functioning of the spraying device of the invention.

Said functioning is as follows.

The spraying device is attached to the inner surface of the lid of a toilet. When the lid is closed, a specific tilt sensor (10) detects the new, horizontal position of the device and the device starts to operate after a delay of 10 seconds: the control unit (11) sends a signal to the motor (12) that drives the sequential drive mechanism (13). Said sequential drive mechanism comprises several gears that sequentially operate the fluid pump (14) and the rotatable nozzle (15).

For delivering the cleaning liquid, the sequential drive mechanism first operates the fluid pump to suck the desired amount of cleaning liquid from the cartridge or reservoir (16). After the liquid has filled the pump's chamber, the piston of the pump pressurizes the liquid so as to push it in the direction of the rotatable nozzle (15). Here the cleaning liquid passes through a very fine orifice which atomizes the solution into a sprayed aerosol. The nozzle in said orifice has a diameter of 0.2 mm whereas the pressure drop over the orifice is about 4 bar. Furthermore, the mass flow rate through the rotatable nozzle is about 0.8 ml/second.

After the first spray shoot has thus been delivered into the toilet bowl the sequential drive mechanism rotates the nozzle (15) over an angle of 72 degrees.

As soon as the nozzle completes this rotating movement, the drive mechanism (13) sequentially operates the pump (14) so as to deliver another spray shoot from the new position. These sequential spraying and moving operations are repeated five times during a full spray cycle. It follows that during a complete spray cycle, the nozzle (13) rotates over an angle of 360 degrees, while delivering a total of five spray shoots. An electronic assembly (shown in FIG. 1) regulates the spray cycle. Said electronic assembly is able to automatically start the spray cycle and to count the number of spray shoots for automatically terminating the spray cycle after five spray shoots. Each shoot delivers about 0.1 ml of cleaning liquid into the inner volume of the toilet bowl; so, the total cleaning fluid delivery per spray cycle is about 0.5 ml. Thanks to the very fine particle size of the sprayed liquid particles of each spray shoot, this tiny amount of 0.5 ml cleaning fluid was found to be sufficient to disinfect the internal volume of the toilet bowl and to cover and disinfect the complete inner surface of the toilet bowl, even under the rim thereof.

The complete spray cycle lasts for about 5 seconds at the end of which the toilet will be disinfected and ready for use again.

Figure 3:
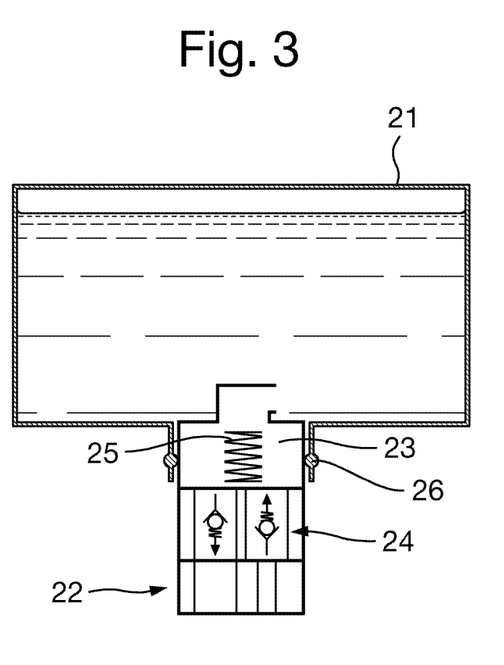

FIG. 3 contains a preferred reservoir, also called cartridge, containing the cleaning fluid and suitable for use in the spraying device of the invention. This cartridge is composed of several parts including a cartridge body (21) for holding about 45 ml of cleaning liquid. Said cartridge body is closed with a cap assembly (22) comprising a sump (23), two check valves (24) and a spring (25). The cap is secured to the cartridge body with a permanent one-time snap feature (26).

This assembly is also child-proof so as to prevent unintended access to the solution.

The two separate check valves are used for controlling the path of the cleaning fluid into the pump assembly of the device and the air path into the cartridge.

Figure 4:
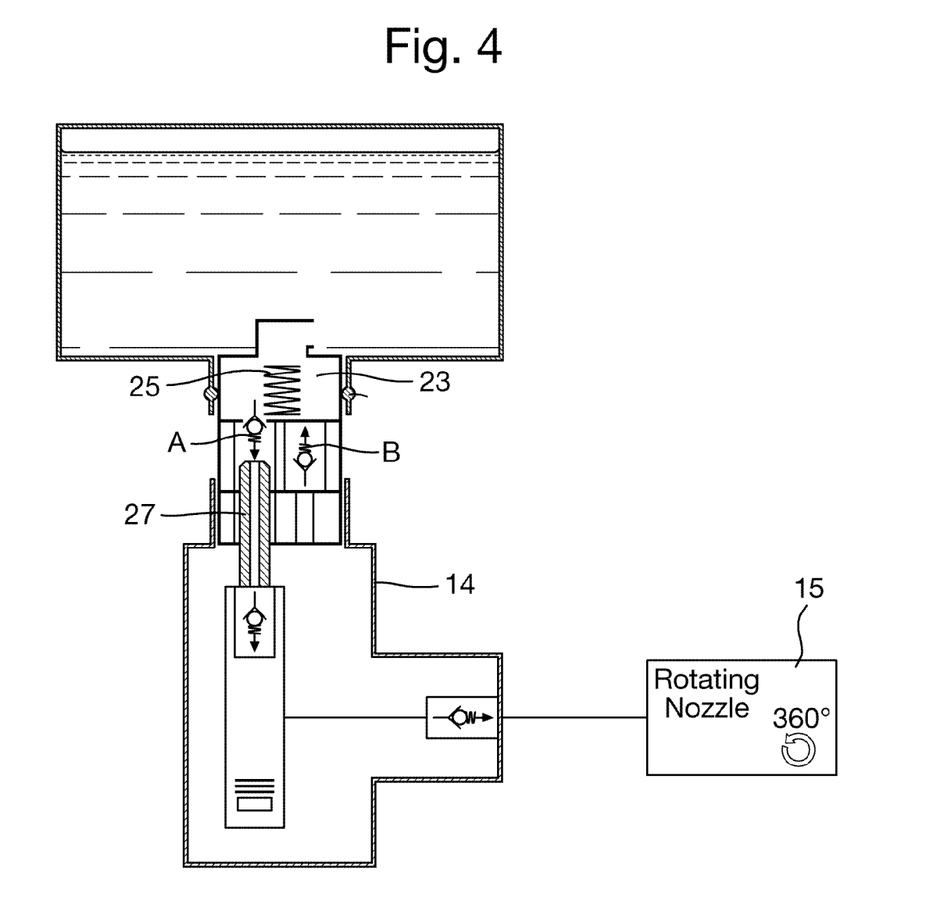

FIG. 4 shows the situation in which the cartridge is inserted into the spraying device. It can be seen that the fluid check valve A is opened (indicated by an arrow) by a small post (27) that presses the valve open and allows cleaning fluid to exit the cartridge assembly.

It is noted that the fluid check valve A remains open all the time the cartridge stays inserted into the spraying device. The air entry check valve B, on the other hand, can only be opened by negative pressure created inside the cartridge as a result of cleaning fluid being removed by the pump assembly (14). The spring (25) is used to keep in place both the fluid and air check valves A and B and to apply the necessary closing force on said valves.

The sump creates an internal space in the cap assembly for fluid to be drained into said sump when the toilet lid is in the vertical position.

Figure 5:
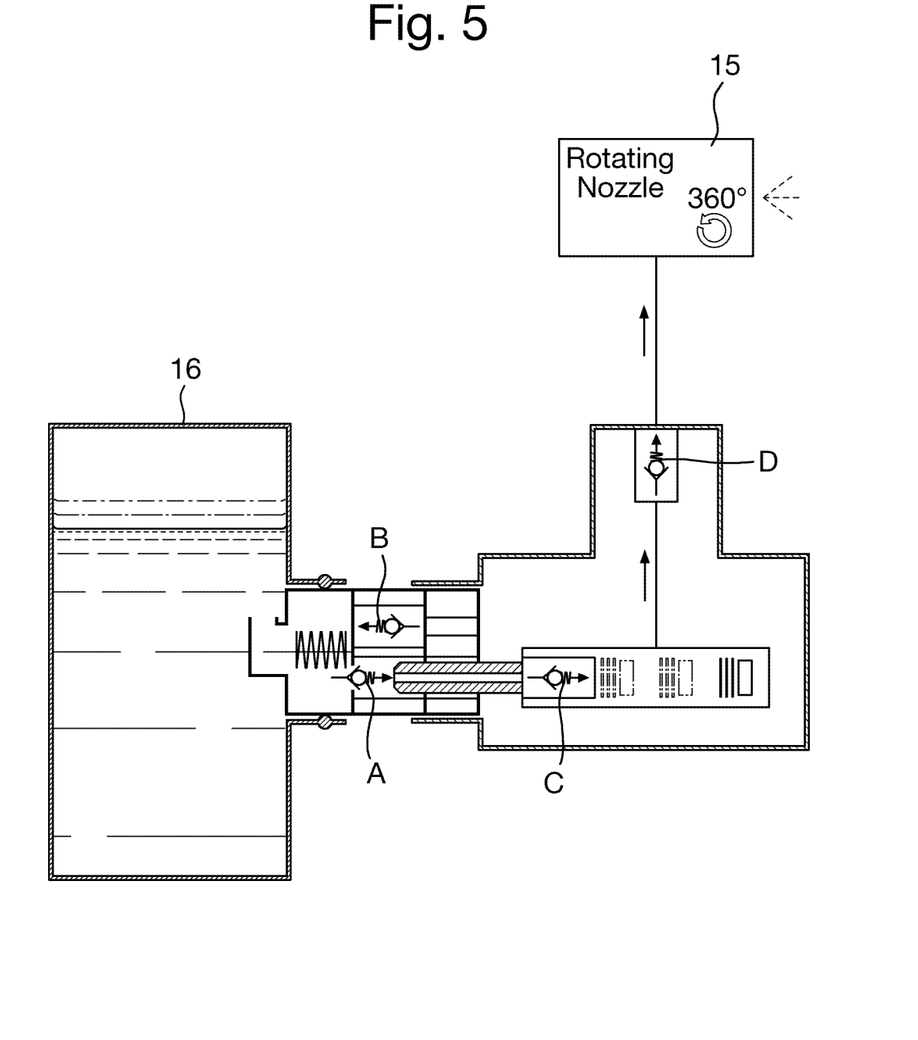

When the toilet lid is placed into the horizontal position, the cleaning fluid level in the sump will always remain higher than the fluid level in the cartridge as fluid is removed during use. (as shown in FIG. 5).

When the pump starts working (device in horizontal position) the fluid check valve C on the pump side of post (27) opens automatically, owing to the vacuum pressure created by the movement of the piston inside the pump chamber (down stroke). This allows the cleaning fluid to reach the piston chamber. Here the fluid is pushed by the upstroke of the movement of the piston up to the rotatable nozzle where it is dispensed as a sprayed aerosol.

It is important to note that the two check valves C and D that regulate the fluid flow inside the pump, operate sequentially and not simultaneously. In particular, when the vacuum force generated by the down stroke of the piston opens the first check valve C the other one stays closed, allowing the fluid to fill the chamber of the pump. Subsequently, during the upstroke of the piston the reverse force keeps check valve C closed while opening check valve D, so as to allow the fluid to reach the nozzle.

As the cleaning liquid is sucked out of the cartridge by the pump, negative pressure is generated inside the cartridge. When this negative pressure reaches a certain level, it opens the air entry check valve B thus allowing ambient air to flow into the interior of the cartridge so as to redress the pressure balance.

The present invention will now be further illustrated in the following non-limiting examples.

EXAMPLE 1

In this example experiments were carried out so as to find the beneficial effect of the spraying device of the invention when compared with a spraying device having simultaneous pumping and nozzle rotating action.

To this end, the electric power consumed by a prototype spraying device of the invention (having sequential pumping and rotating action) as well as a comparative spraying device (having simultaneous pumping and rotating action) was measured.

The following results were obtained:

| Pump configuration | Peak power consumed | Efficiency |
| --- | --- | --- |
| Simultaneous pump & rotate | 5.5 watt | 23% |
| Sequential pump & rotate | 4.5 watt | 28% |

It follows from the above results that the sequential system according to the invention is more efficient and requires 1 watt less power that the simultaneous system of the prior art. This significant benefit is unexpected as the rotating nozzle requires only very little power to rotate.

EXAMPLE 2

In this example, experiments have been carried out with a spraying device of the invention (producing an aerosol having an average Dv50 particle size of 50 microns) as well as a modified spraying device. The aerosol produced by the modified spraying device has an (much higher) average Dv50 particle size of 100 microns. It is further noted that this modified spraying device only differs from the spraying device of the invention with regard to the average particle size of the aerosol produced.

A test was designed to check if the sprayed aerosol delivered by each of these spraying devices is able to reach and disinfect the under the rim area of the internal surface of a toilet bowl. It was chosen to test the coverage under the rim as this part of the toilet surface is generally difficult to be reached by the sprayed aerosol. For this test, test slides containing a 4 log *escheria coli* bacteria culture were positioned in the cavity under said rim.

Furthermore the following test conditions were applied:

| | |
| --- | --- |
| cleaning fluid used | 0.7 wt % Na hypochlorite in water; |
| spray cycle used | 5 spray shoots of 0.1 ml cleaning fluid |
| contact time before testing bacterial growth | 5 minutes |
| Toilet type | Kolo |

The following results were obtained:
Bacterial growth (log) (in the under the rim area)

|  | Start of test | After spray cycle and 5 min. contact time |
|---|---|---|
| Using device of invention (Dv50 of aerosol: 50 microns) | 4.16 | 1.74 |
| Using modified device (Dv50 of aerosol: 100 microns) | 4.00 | 3.2 |

When considering these results it can be derived that the result, in terms of log reduction of the bacteria culture on the test slides, is 2.42 when using the device of the invention. On the other hand, said result is 0.8 when using the modified device.

It follows that the spraying device of the invention is roughly 3 times more effective than the modified device having regard to the disinfecting performance under the rim of a toilet bowl.

The invention claimed is:

1. An automated spraying device for spraying an enclosure with a liquid cleanser, the device having, a reservoir(16) suitable for containing the liquid cleanser, a pump (14) in fluid communication with the reservoir, a rotatable spray head (15) having an outlet orifice through which cleanser from the reservoir can be expelled during operation of the pump (14) if there is such liquid cleanser in the reservoir, wherein the spraying device also contains an electrical motor drive mechanism (12) for sequentially operating the pump (14) and moving the spray head (15) to modify the direction of the spray there from, such that the spray head (15) is not simultaneously spraying and moving, in that the spray head (15) is suitable for producing an aerosol whereby the Dv50 of the aerosol is in the range of from 30 to 70 micron, and wherein sequential spraying and moving operations are repeated five times during a full spray cycle, such that during the full spray cycle, the spray head (15) rotates over an angle of 360 degrees, while delivering a total of five spray shoots.

2. The spraying device according to claim 1, wherein the enclosure is a toilet bowl.

3. The spraying device according to claim 2, wherein the device contains means for attaching the device to a bottom side of a lid of a toilet.

4. The spraying device according to claim 2, wherein the device can only operate for spraying the toilet bowl when a lid is closed.

5. The spraying device according to claim 2, wherein the device contains a sensor (10) for detecting the position of a lid.

6. The spraying device according to claim 2, wherein the device contains a timer for controlling a duration of operation of the spraying device.

7. The spraying device according to claim 2, wherein the reservoir suitable for containing the liquid cleanser (16) can be refilled or exchanged for another reservoir without having to remove the complete device, a volume of the reservoir being between 5 to 200 ml.

8. The spraying device according to claim 7, wherein the reservoir (16) includes a cap assembly (22) comprising a sump (23) and two check valves (24).

9. The spraying device according to claim 8, wherein the liquid cleanser comprises at least a biocide.

10. The spraying device according to claim 9, wherein the biocide in the liquid cleanser is selected from the group consisting of methanol, ethanol, propanol, butanol, polyhexamethylene biguanide, benzalkomium chloride and hypochlorite.

11. A method for disinfecting and sanitizing the inner volume and surface of a toilet bowl containing airborne micro-organisms and/or viruses generated during and/or after flushing, said method comprising the steps of:

attaching a spraying device as claimed in claim 1 to a bottom side of a toilet lid, closing the lid;

flushing the toilet; and actuating the device, by carrying out the following consecutive steps:

(a) spraying a predetermined amount of the liquid cleanser, followed by, (b) rotating the spray head, and repeating steps (a) and (b) at least five times.

12. Use of a device as claimed in claim 1, for disinfecting and/or sanitizing an inner surface of a toilet bowl after flushing the toilet.

13. The spraying device according to claim 7, wherein the reservoir suitable for containing the liquid cleanser (16) can be refilled or exchanged for another reservoir without having to remove the complete device, a volume of the reservoir being between 15 and 60 ml.

* * * * *